United States Patent [19]

Gagliani

[11] 4,183,839

[45] Jan. 15, 1980

[54] POLYIMIDE RESIN-FORMING COMPOSITION

[75] Inventor: John Gagliani, San Diego, Calif.

[73] Assignee: John V. Long, El Cajon, Calif.; a part interest

[21] Appl. No.: 839,412

[22] Filed: Oct. 5, 1977

Related U.S. Application Data

[62] Division of Ser. No. 674,762, Apr. 8, 1976.

[51] Int. Cl.² ............................................. C08G 73/14
[52] U.S. Cl. .............................. 260/37 N; 260/326 C; 260/326 S; 260/326 N; 525/419; 528/26; 528/125; 528/126; 528/170; 528/311; 528/322
[58] Field of Search ............... 260/47 CP, 47 CZ, 49, 260/65, 78 R, 78 TF, 37 N, 824 R, 857 PA, 857 UN, 326 C, 326 S, 326 N; 528/26, 125, 126, 170, 311, 322

[56] References Cited

U.S. PATENT DOCUMENTS

| | | | |
|---|---|---|---|
| 3,852,106 | 12/1974 | Incremona et al. | 117/218 |
| 3,959,233 | 5/1976 | Hanson et al. | 260/77.5 R |
| 4,041,065 | 8/1977 | Lindberg et al. | 260/47 CZ |
| 4,066,631 | 1/1977 | Dimmig | 260/78 R |
| 4,069,208 | 1/1978 | Lange | 260/75 N |

*Primary Examiner*—Lester L. Lee
*Attorney, Agent, or Firm*—Haight & Huard

[57] ABSTRACT

Polyimides of the formula

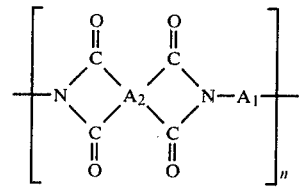

Methods of making and polymerizing precursors for such polymers. Coating and adhesive compositions including constituents which can be converted into polyimides with the foregoing structure. Methods of making and using the compositions. Adhesion promoters for such compositions which are reaction products of aromatic dianhydrides and cyclic oxoimines, and methods of producing and using the adhesion promoters.

10 Claims, No Drawings

POLYIMIDE RESIN-FORMING COMPOSITION

This is a division, of application Ser. No. 674,762, filed Apr. 8, 1976.

In one aspect the present invention relates to novel polyimides which are obtained by effecting an exchange reaction between a cyclic aliphatic bisimide and an aromatic diamine.

In other aspects our invention relates to the bisimides, which are themselves novel, to novel methods of forming such compounds, and to novel methods for converting the bisimides and diamines to imide polymers.

In still other aspects our invention relates to novel coating and adhesive compositions which are solutions of bisimides and diamines as aforesaid and to the making and use of such compositions.

Finally, our invention relates to novel adhesion promoters which are reaction products of tetracarboxylic dianhydrides and primary amine terminated silanes, to the making of the promoters, and to their use.

The novel imide forming materials we have invented are mixtures or adducts of one or more meta- or para-substituted aromatic diamines and an N-substituted, aliphatic, bisimide with terminal carboxylic groups. The bisimide and the diamines are present in essentially stoichiometric proportions.

Preferred are those bisimides of the formula

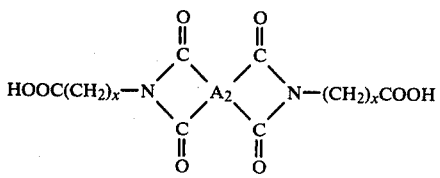

where x is 4 to 6, and $A_2$ is

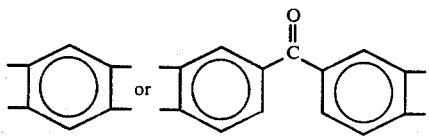

Our novel bisimides are made by reacting an aromatic tetracarboxylic acid dianhydride with a cyclic amide or oxoimine; i.e., a compound of the formula

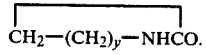

A wide variety of dianhydrides can be employed in practicing our invention. Suitable dianhydrides include those disclosed in U.S. Pat. No. 3,282,897 issued Nov. 1, 1966, and U.S. Pat. No. 3,310,506 issued Mar. 21, 1967, both incorporated herein by reference.

As suggested above, however, the preferred dianhydrides are pyromellitic dianhydride and 3,3',4,4'-benzophenone tetracarboxylic acid dianhydride (BTDA). The preference for these two dianhydrides is based principally upon their availability in commercial quantities at reasonable prices.

The preferred oxoimine is caprolactam,

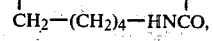

although those lactams with five- and seven-membered rings can also be used. Caprolactam reacts with the preferred dianhydrides to form benzophenonetetracarboxylimide, N,N'-pentamethylene, 5,5'-dicarboxylic acid and pyromellitimide-N,N'-pentamethylene, 5,5'-dicarboxylic acid respectively.

The bisimide is prepared by adding the dianhydride to the oxoimine and heating the mixture at 170°–200° C. until imidization is complete. This requires 20–60 minutes.

It is important, in preparing the bisimide, that the ratio of cyclic oxoimine to dianhydride be in the range of 1:1 to 8:1. Outside of this range solubility of the bisimide in the solvent cannot be insured.

Excess oxoimine has the advantage of reducing the viscosity of the bisimide which makes it easier to handle. Oxoimine to dianhydride ratios in the range of 2.3:1 to 2.7:1 have been found particularly advantageous from this viewpoint with the 2.7:1 ratio being preferred.

A variety of aromatic diamines may also be used in preparing our novel imide-forming materials, and aliphatic groups may be present in the molecule although aromatic diamines of this character are preferably avoided in high temperature applications because the aliphatic moiety has an adverse effect on thermal stability.

Suitable diamines include, but are not limited to:
meta-phenylene diamine
para-phenylene diamine
4,4'-diaminodiphenyl ether
4,4'-diaminodiphenyl sulfone
3,3'-diaminodiphenyl sulfone
4,4'-diaminodiphenyl sulfide
4,4'-diaminodiphenyl methane
mixtures of two or more of the above-listed diamines Other diamines which can be employed, alone and in various admixtures, are disclosed in U.S. Pat. Nos. 3,282,897 and 3,310,506 and in U.S. Pat. No. 3,391,120, hereby also incorporated herein by reference.

The polyimide forming material is prepared by adding the cyclic bisimide to a solvent and stirring until solution is complete. The aromatic diamine or diamine mixture is then added at a temperature in the range of 20°–60° C. and the mixture stirred until solution is complete.

The bisimides are soluble in a variety of inert polar and nonpolar solvents, and the formation of the bisimide can be carried out in any of these. Solvents which are preferred because of their relatively low cost, wide availability, low boiling points, and possession of minimal undesirable properties include:
Dimethyl acetamide
Dimethyl formamide
N-methylpyrrolidone
Acetone
Methylisobutyl ketone
Methylethyl ketone
Ethyl alcohol
Benzene
Xylene The polyimide forming material yielded by the novel procedure just described is a viscous fluid containing an intimate, unpolymerized mixture or adduct of N-substituted cyclic bisimide dicarboxylic acid and diamines which is capable of being converted to a high molecular weight polymer by the application of heat.

Those presently most highly preferred precursors have the formula

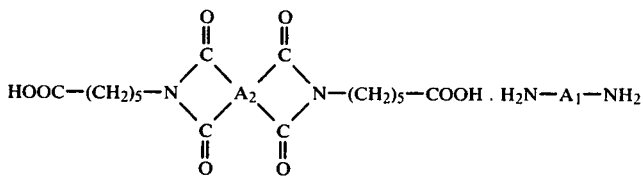

where A₁ is selected from the group consisting of

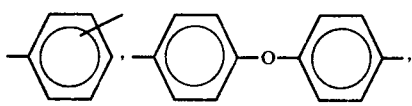

and

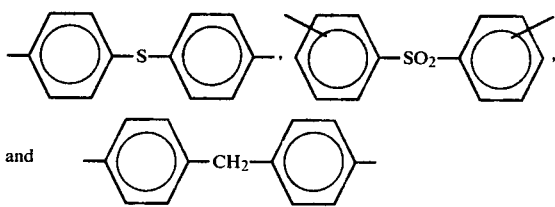

and A₂ is

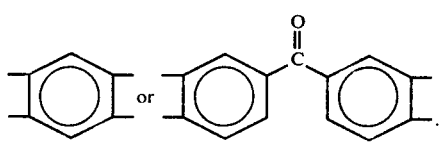

If desired, the solvent can be evaporated from the precursor to reduce it to solid form. This is not necessary, however, as the solutions are stable at room temperature and can be stored indefinitely.

Furthermore, these novel solutions can be applied to a variety of substrates including stainless steels, aluminum, titanium, copper, steel and other metals; glasses; and plastics and to substrates with complicated geometrical configurations by such conventional and relatively inexpensive techniques as dip and spray coating. Such solutions are therefore valuable coating compositions.

The novel precursors we have invented can be converted to high molecular weight polyimides by the application of heat. Under the influence of heat the polyimide is formed via an exchange reaction between the N-substituted bisimide dicarboxylic acid and the aromatic diamine or diamines and the liberation of a carboxy terminated aliphatic amine as shown by the following, exemplary reaction:

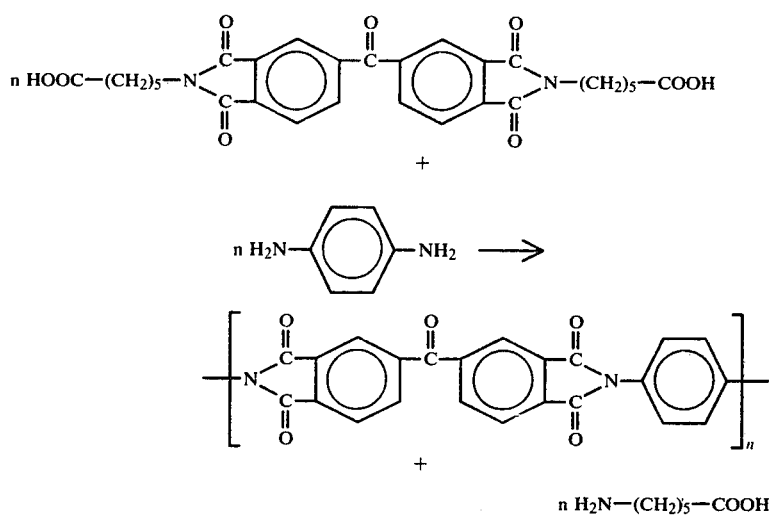

wherein n is a positive integer.

The foregoing reaction is carried out by heating the precursor at a temperature in the range of 177°–316° C. for 30 minutes to 5 hours, depending upon the temperature employed. Suitable reaction parameters are 5 hours at 177° C., 3 hours at 232° C., 2 hours at 260° C., and 30 minutes at 316° C.

Alternatively, staged curing temperatures can advantageously by employed, especially in laminating applications. One exemplary curing cycle of this character is 2 hours at 177° C., 3 hours at 204° C., and 1 hour at 316° C.

The polymers have excellent adhesion characteristics on metals and even on plastics and glasses. They do not absorb water and possess excellent resistance to salt sprays, high temperature resistance, abrasion resistance, and the like.

Our novel coating materials are preferably applied in thicknesses of not more than 1–3 mils in single application operations. Thicker applications tend to result in pinholes and other flaws.

Thicker coatings can, however, readily be obtained by building up the coating thickness in two or more stages.

A second lamina can be bonded to the substrate by heating the two laminae to temperatures as low as 177° C. under pressures as low as 50 psig for approximately one second. Bonding speeds in the range of 2-12 feet per minute are employed.

The peel strength and other mechanical properties of the adhesive at room and elevated temperatures are excellent.

The adhesion characteristics of the coating or adhesive can be improved by the use of selected additives and/or adhesion promoters. The preferred, and novel, adhesion promoters are reaction products of an aromatic acid dianhydride and a primary amine terminated alkoxy silane. We have not as yet identified the exact structure of the reaction product.

The preferred dianhydrides are 3,3′,4,4′-benzophenonetetracarboxylic acid dianhydride and pyromellitic dianhydride. The preferred silane is aminopropyl triethoxy silane.

However, other dianhydrides including those disclosed in the patents incorporated by reference above can be employed. Similarly, we contemplate the use of other silanes excepting those having other than primary amine terminal groups.

The silane is reacted separately with the dianhydride in a polar solvent at a temperature of 25° to 60° C. An excess of dianhydride ranging from one to 50 percent is employed to keep the promoter fluid and homogeneous. Typically, the excess will be on the order of seven percent.

The resulting mixture is added to the bisimide diamine solution at a temperature in the range of 50° to 60° C. with stirring until the resulting mixture becomes homogeneous.

Alternatively, the silane can be mixed with the aromatic diamine or diamines. The resulting mixture is incorporated in the polyimide precursor under the same conditions as the diamines alone.

Our novel adhesion promoters are used in amounts which result in up to 0.1 molecular parts of silane to one molecular part of diamine or diamines being present in the final composition. Higher proportions of the silane produce greater adhesion but cause brittleness and are accordingly used only where more brittle coatings can be tolerated.

The novel adhesion promoters just described react with the polymer as it is formed through the exchange reaction described above. This results in reaction sites capable of producing secondary or covalent bonds with a substrate and thereby increasing the tenacity of the bond between polymer and substrate.

The novel adhesion promoters just described are useful independently of the novel polyimides disclosed herein. For example, they can also be used as promoters for epoxy and polyester resins.

Our novel coating and adhesive compositions possess an outstanding degree of wettability. As a consequence, a virtually limitless variety of organic and inorganic fillers can be added to the composition to promote wanted characteristics in the polymer and/or to provide it with additional desirable characteristics. Fillers which we have successfully incorporated include: fluorinated hydrocarbons (e.g., Teflon), aluminum, chromium oxide, aluminum phosphate, aluminium chromate, magnesium phosphate, and mixtures of the foregoing.

The addition of the filler is straightforward. It is simply milled into the precursor as in a ball mill at room temperature until the mixture becomes homogeneous.

The amount of filler will of course vary from application-to-application depending upon the particular filler, the purpose for which it is incorporated, and other factors. In general, filler-to-resin ratios as high as 2.5 parts by weight of filler to one part by weight of resin can be employed without resin starvation and a consequent formation of a soft and porous coating although a 1:1 ratio in general tends to give the best results. Higher ratios can be employed in applications where a resin starved composition is wanted or acceptable although such compositions are in general not employed to any great extent in the applications for which our novel compositions are best suited. Ratios lower than 0.1:1 seem to have little if any potential.

One particular valuable filler is a mixture of 8 to 20 parts aluminum hydroxide, 20 to 60 parts chromium trioxide, 15 to 50 parts of magnesium oxide, and 150 to 300 parts of phosphoric acid used in a ratio of one part by weight of filler per part of precursor composition. This filler imparts outstanding high temperature resistance to the final coating or adhesive.

Powdered glasses can be used with similar results.

Other exemplary fillers include chromic oxide, aluminum, and magnesium phosphates, aluminum, copper, steel, and fluorocarbon resins.

Flow control agents and wetting agents can also be added to the precursor composition to improve the properties of the coating or adhesive.

Our novel, polyimide coating and adhesive compositions are completely unlike any of which we are aware and have a number of advantages not possessed by those heretofore available.

With exceptions of little commercial importance those heretofore proposed polyimides of which we are aware are formed by a process which involves condensation reactions between a tetracarboxylic acid and a primary diamine rather than an exchange reaction like our invention. The condensation products come off as gases, leaving pinholes and bubbles in the coating. The coatings we produce are in contrast almost or entirely free of such imperfections.

Stability of the solution is also a distinguishing feature of our novel compositions. The conventional compositions are solutions of polyamic acids which are notoriously unstable. It is therefore impractical to prepare the composition significantly in advance to the time that it is to be used.

Those of our precursors with reactive fillers such as magnesium carbonate have a shorter shelf life than those precursors which do not contain fillers. Even at this, however, our novel precursors have substantially longer shelf lifes than other polyimide precursors containing the same fillers.

Furthermore, because our novel compositions possess high solubility, they can be applied by a wide variety of coating techniques including those widely used ones mentioned above. In contrast, conventional compositions have to be applied by a roll coater in commercial practice. Even then, the uncured coatings are brittle and have poor adhesion, especially to non-metallic surfaces; and more expensive solvents have to be employed.

Also, as mentioned above, our novel coatings can be applied to sharp edges and to complex shapes. This is due primarily to their wettability and adhesion. Conventional compositions in contrast, are generally useful only for coating a single surface of simple shape because of their poor wettability and low adhesion and because they tend to have poor drying properties.

Furthermore, because of their poor wettability, the inclusion of fillers in prior art polyimide coating compositions is in general impractical.

Resistance to hydrophilic attack is another distinguishing feature of the novel imide polymers disclosed herein. In fact, these polymers are even resistant to attack by caustic materials, an advantage definitely not possessed by conventional polyimides.

From the foregoing it will be apparent to the reader that one important and primary object of the invention is the provision of novel polyimides which are exchange reaction products of N-substituted cyclic bisimides and aromatic diamines.

Another primary object of our invention resides in the provision of novel coatings and adhesives which are composed at least primarily of imide polymers obtained as aforesaid, and in the provision of novel imide-forming compositions therefor.

A related and also primary object of our invention resides in the provision of novel polyimide precursors which are substantially equimolar and intimate mixtures or adducts of N-substituted cyclic bisimides and aromatic diamines and in the provision of novel methods for making the precursors and the bisimides and for using the precursors and converting them to imide polymers.

Yet another important and primary object of the invention resides in the provision of novel adhesion promoters.

And yet another primary object of our invention resides in the provision of novel techniques for modifying the physical properties of imide polymers.

Additional and also important objects of our invention include the provision of polyimides and polyimide adhesives and coatings:

(1) which are highly adherent to both metallic and non-metallic surfaces, to sharp edges, and to geometrically complex shapes;

(2) which are non-hydrophilic, have high resistance to salt sprays and abrasion, and possess excellent high temperature resistance;

(3) which have excellent mechanical properties, including peel strength, at both room and elevated temperatures;

(4) which are essentially free of pinholes, bubbles, and similar defects;

(5) which are capable of bonding two laminae together by the application of modest pressures at modest temperatures.

Further important objects of the invention reside in the provision of imide-forming coating and adhesive compositions:

(6) which have a long shelf life;

(7) which, before curing, will adhere to a variety of metallic and non-metallic substrates and to sharp edges and complex surfaces;

(8) in which fillers can be readily incorporated in a straightforward manner to modify the properties of the polymer into which the precursor is converted;

(9) which can be applied by a variety of conventional coating techniques;

(10) which are essentially stoichiometric mixtures or adducts of N-substituted cyclic bisimides and aromatic diamines in a polar or non-polar solvent;

(11) which, in conjunction with the preceding object, contain imide-forming constituents that are highly soluble in, and therefore permit the use of, low boiling point, relatively inexpensive solvents.

Additional important objects of the present invention include:

(12) the provision of novel, N-substituted bisimides which are reaction products of an aromatic acid dianhydride and a cyclic oxoimine;

(13) the provision of adhesion promoters capable of so reacting with the polymers with which they are associated as to make the polymer capable of forming chemical bonds with a substrate;

(14) the provision of adhesion promoters which are the reaction products of aromatic acid dianhydrides and primary amine terminated silanes and the provision of methods for making such promoters.

Other objects and advantages and additional novel features of our invention will be apparent to those skilled in the relevant arts from the foregoing description of the invention, from the appended claims, and from the following examples, which are intended only to illustate and not restrict the scope of the invention.

EXAMPLE I

A precursor of the character we contemplate was prepared as follows:

3,3',4,4'-Benzophenonetetracarboxylic acid dianhydride (BTDA) (322 g, 1 M) and caprolactam (30 g, 2.7 M) were placed in a two liter flask, heated to a temperature of between 170° and 180° C., and maintained at that temperature for 30 minutes. Thereafter, the mixture was cooled to 140° C., dimethyl formamide (500 g) was added, and the mixture was stirred until homogeneous.

The mixture was further cooled to 50°-60° C. At this point BTDA (8.5 g, 0.035 M) was added, and the mixture was stirred for 5 minutes.

This was followed by the addition of aminoproplytriethoxy silane (15.45 g, 0.05 M). The mixture was stirred for 10 minutes at 50°-60° C. 4,4'-Diaminodiphenyl ether (200 g, 1M) was added; and the mixture stirred for 10 minutes at 50°-60° C., producing a viscous liquid. To this was added 800 g of a mixture containing equal parts by weight of acetone, methylisobutyl ketone, ethyl alcohol, and dimethylacetamide. The mixture was then stirred at 20°-60° C. for 1 hour, becoming homogeneous.

The resulting product is useful as a coating composition and possesses an indefinite shelf life.

EXAMPLE II

The composition of Example I was sprayed onto a 410 stainless steel panel using a De Vilbiss spray gun with an F fluid tip and an air pressure of 50 psig.

The composition was dried at 121° C. for 10 minutes, evaporating the carrier and producing a tough, hard, abrasion resistant coating.

Thereafter, the coating was cured at a temperature of 316° C. for 30 minutes to effect the imide exchange reactions. The coating became even harder and was demonstrated to be resistant to solvents, oils, acids, and salt sprays and to elevated temperatures.

EXAMPLE III

It was pointed out above that the properties of resinous coatings can in many applications be improved by the incorporation of selected additives or fillers, that this approach is of little value as far as conventional polyimides are concerned because of their poor wettability, and that this deficiency of heretofore available polyimide coatings is not present in the novel polyimide coating materials we have invented.

To demonstrate this, 13 parts by weight of aluminum hydroxide, 40 parts of chromium trioxide, 30 parts of magnesium oxide, and 240 parts of phosphoric acid were blended at 100° C. Seventy parts by weight of dimethylformamide was miled into this mixture; and the resulting mixture was blended with 400 parts of the resin of Example I.

The composition thus obtained was spray coated onto a stainless steel panel as described in Example II; and the composition was cured to effect the imide exchange reactions at 316° C. for 30 minutes, yielding a polyimide of the formula

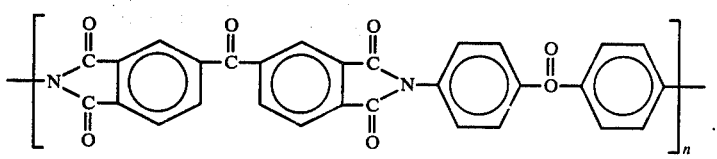

wherein n is a positive integer.

The coating was found to be resistant to sustained temperatures of 316° C. with periodic excursions to temperatures as high as 538° C.

The procedure was repeated using a conventional polyimide resin solution (Amoco Al-1137) and a resin made by reacting one mole of BTDA with one mole of 4,4'-diaminodiphenyl oxide in 1000 ml of dimethyl acetamide. In both cases the resin separated from the filler, producing an unsatisfactory coating.

EXAMPLE IV

The procedure described in Example III was repeated using as an additive or filler a composition containing 30 parts of the mixture first described in Example III, 70 parts of dimethyl acetamide, and 30 parts of finely pulverized aluminum powder. This mixture was added to 400 parts of the resin of Example I, and the product was coated onto a stainless steel panel and cured as described in Example II.

The cured coating was hard and resistant to temperatures as high as 316° C. periodically increased to 538° C.

The same experiment was repeated using the conventional polyimide resin solution (Amoco Al-1137). Again, the resin precipitated out due to incompatibility.

EXAMPLE V

To demonstrate how thicker coatings than that resulting from the procedure described in Example II can be obtained, that procedure was repeated applying three 3–5 mil coatings of the Example I formulation and drying the coating at 93° C. in an air circulating oven after each application. After the third application had been dried, the coating was cured for 1 hour at 149° C., 2 hours at 232° C., 30 minutes at 260° C. and 30 minutes at 316° C. A fully cured, homogeneous coating was obtained.

EXAMPLE VI

To demonstrate that other aromatic diamines can be used in forming our novel polyimide precursors, the procedure of Example I was repeated using 248 g (0.1 M) of 4,4'-diaminodiphenyl sulfone in place of the 4,4'-diaminodiphenyl oxide. The final resin solution or coating composition was stable at room temperature and yielded light colored coatings.

EXAMPLE VII

It was also pointed out above that mixtures of aromatic diamines can be used in making polyimides in accord with the principles of the present invention instead of a single diamine.

The suitability of a diamine mixture was demonstrated by repeating the procedure described in Example I using a mixture of meta-phenylene diamine (59 g, 0.5 M) and para-phenylene diamine (59 g, 0.5 M) in place of the 4,4'-diaminodiphenyl oxide.

The final resin or coating solution was stable at room temperature and yielding coatings which possessed outstanding abrasion resistance.

Abrasion resistance was demonstrated by a standard sand abrasion test using a 150 ft/sec sand velocity. The coating maintained its surface properties and compared favorably with the best fluorocarbon coating recommended for erosion and abrasion environments (Dupont's Viton B).

In a Taber abrasion test a los per revolution of 0.21 milligrams with a H-22 wheel and 1000 gram load was measured. Viton coatings had an only slightly better loss in the same test.

EXAMPLE VIII

To demonstrate how we employ wetting and flow control agents and that aromatic anhydrides other than BTDA dianhydride can be employed in making the novel copolyimides of the present invention, pyromellitic dianhydride (218.12 g, 1 M) and caprolactam (304 g, 2.7 M) were placed in a two liter flask, heated to a temperature of between 170°–180° C., and maintained at that temperature for 30 minutes. Thereafter, the mixture was cooled to 140° C.; and dimethyl acetamide (500 g) was added and the mixture stirred until homogeneous.

The mixture was then further cooled to 50°–60° C. At this point 4,4'-diaminodiphenyl sulfide (216.37 g, 1 M) was added and the mixture stirred for 10 minutes at 50°–60° C. To the resulting viscous liquid was added 800 g of an equal weight mixture of acetone, methylisobutyl ketone, ethyl alcohol, and dimethyl acetamide. The mixture was stirred at 20°–60° C. for 1 hour. General Electric SR-82 flow control agent (1.5 g) and Dow Corning DC-11 wetting agent (1.5 g) were added to the mixture and stirred for an additional 30 minutes to complete the process.

The final coating resin can be stored indefinitely.

EXAMPLE IX

As indicated above, our invention also embraces novel adhesion promoters which are reaction products of BTDA or pyromellitic anhydride and a primary amine terminated silane.

Adhesion promoters of this character were prepared by placing aminopropyltriethoxy silane (53.0 g, 0.24 M) and 136 g of dimethylacetamide in a two liter flask and stirring the mixture. BTDA (83.0 g, 0.256 M) was then added over periods varying from 10 to 60 minutes. The mixtures were stirred for an additional 60 minutes at temperatures in the 25°–60° C. range to drive the reactions to completion.

Adhesion promoters thus produced, by themselves, have a shelf life of approximately two days and must be used within this period.

EXAMPLE X

To demonstrate the use of an adhesion promoter as described in Example IX, a polyimide precursor was prepared by the following procedure.

Caprolactam (45.2 g, 0.4 M) and BTDA (16.1 g, 0.05 M) were placed in a two liter flask, heated to a temperature of 170°–180° C., and maintained at that temperature for 30 minutes. Thereafter, the mixture was cooled to 140° C., and dimethyl acetamide (200 g) was added and the mixture stirred until it became homogeneous.

The mixture was further cooled to 50°–60° C., and 4,4'-diaminodiphenyl ether (30 g, 0.15 M) and 10.8 g (0.005 M) of an adhesion promoter as described in Example II were added. BTDA (30.6 g, 0.095 M) was then added, and the mixture was stirred for 1 hour at 50°–60° C. The resulting composition was a dark viscous liquid which remained stable for several months.

EXAMPLE XI

Adhesion promoters as disclosed herein can also be used to advantage in formulations as described in Example VIII.

To show how they are employed and an alternate technique for making the promoters, the procedure described in Example VIII was repeated, using the same ingredients and adding the adhesion promoter after reaction of the pyromellitic dianhydride and caprolactam and after the addition of the dimethyl acetamide. Specifically, pyromellitic dianhydride (5.45 g, 0.025 M) was added to the solution after cooling to 50°–60° C., and this was followed by the addition of aminopropyl triethoxy silane (15.45 g, 0.05 M). The mixture was stirred for 10 minutes at 50°–60° C. Addition of the 4,4'-diaminodiphenyl sulfide, the mixture of solvents, the SR-82 and the DC-11 followed.

The final coating resin produced in this manner can be stored idefinitely.

EXAMPLE XII

The advantages of employing our novel adhesion promoters was demonstrated by applying a coating composition as described in Example VIII to a Kapton film (Dupont) using conventional roll-to-roll coating equipment. The composition was dried at 93° C. for 10 minutes in a heated duct, producing a Kapton tape which is stable at room temperature for indefinite periods and which is flexible and rubbery.

The tape can be laminated to copper and aluminum foils and to Kapton film by passing it between rolls under a pressure of 50 psi and at a temperature of 121° C. The laminate is post-cured for 2 hours at 149° C. and 1 hour at 316° C. to increase the bond strength.

The laminate is resistant to temperatures as high as 427° C. and possesses a peel strength of 6–8 lbs/inch at 316° C.

As discussed above and demonstrated by the working examples, the polyimides we have invented are particularly useful as coatings and adhesives. This is by no means the only purposes for which these materials can be advantageously employed, however. Accordingly, the discussion of coating and adhesive applications is in no way intended to limit the scope of protection to which we consider ourselves entitled.

Our invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed and desired to be secured by Letters Patent is:

1. A process for preparing a polyimide of the formula:

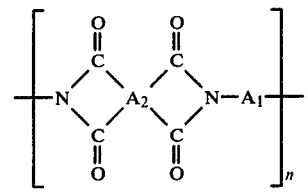

wherein $A_1$ is a divalent aromatic radical selected from the group consisting of

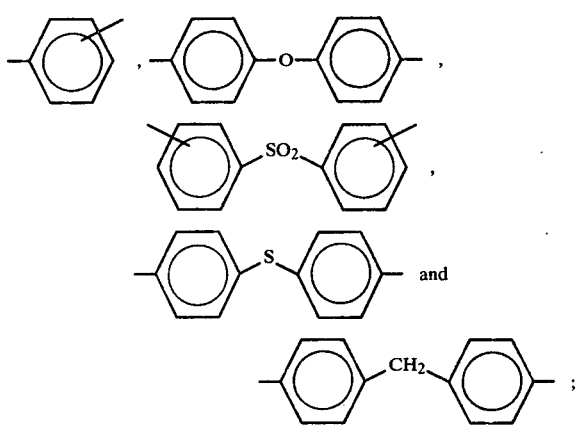

$A_2$ is a tetravalent, aromatic radical of the formula

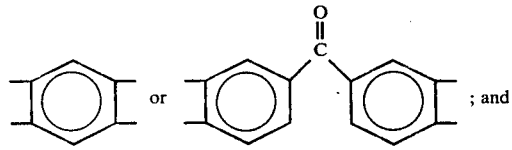

n is a positive integer;

which comprises heating a homogeneous solution consisting essentially of an inert solvent and a stoichiometric adduct of the formula:

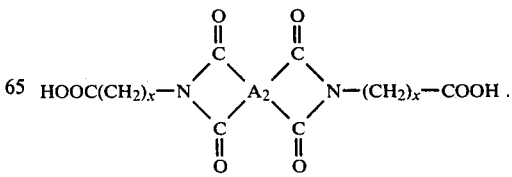

$$H_2N-A_1-NH_2$$

wherein x is 4–6 and $A_1$ and $A_2$ each have the above-indicated values to form said polyimide.

2. A process according to claim 1, wherein the bisimide is benzophenonetetracarboxylimide-N,N'-pentamethylene-5,5'dicarboxylic acid, the diamine is 4,4'-diaminodiphenyl ether and the solvent is a mixture of equal parts of acetone, dimethyl formamide and methyl ethyl ketone.

3. A process according to claim 2, wherein said composition is heated to a temperature of 177°–316° C.

4. A process according to claim 2, wherein said composition further comprises about 0.1 to 2.5 parts by weight of homogeneously admixed filler per part of imide-forming material.

5. A process according to claim 4, wherein the filler is an aluminum hydroxide, magnesium oxide, chromium oxide, aluminum phosphate or magnesium phosphate; phosphoric acid, aluminum; copper; steel; a fluorocarbon resin; or a mixture of two or more of the foregoing.

6. A process according to claim 4, wherein said composition further comprises up to 0.1 parts of an adhesion promoter per molecular part of amine or amine mixture, said adhesion promoter being the reaction product of a dianhydride and a primary amine-terminated silane.

7. A process according to claim 6, wherein the dianhydride is 3,3',4,4'-benzophenonetetracarboxylic acid dianhydride and the silane is aminopropyltriethoxy silane.

8. A polyimide obtained according to the process of claim 1.

9. A polyimide obtained according to the process of claim 4.

10. A polyimide obtained acording to the process of claim 6.

* * * * *